United States Patent [19]

Pierce et al.

[11] Patent Number: 4,898,167

[45] Date of Patent: Feb. 6, 1990

[54] AIDS PROTECTION VENTILATION SYSTEM

[75] Inventors: Richard S. Pierce, San Clemente; Willem J. Van Leeuwen, Chino, both of Calif.

[73] Assignee: Pakam Data Systems Inc., Wilmington, Del.

[21] Appl. No.: 193,895

[22] Filed: May 13, 1988

[51] Int. Cl.$^4$ .................... A62B 9/02; A61M 16/08; A61M 16/20

[52] U.S. Cl. ...................... 128/205.16; 128/205.24; 128/205.12; 128/205.11

[58] Field of Search ................ 128/204.18, 205.13, 128/205.16, 205.19, 205.14, 205.25, 205.11, 205.12, 205.24

[56] References Cited

U.S. PATENT DOCUMENTS

| | | | |
|---|---|---|---|
| 1,202,125 | 10/1916 | Tullar | 128/205.13 |
| 2,073,192 | 3/1937 | Connell | 128/205.13 |
| 2,428,451 | 10/1947 | Emerson | 128/205.13 |
| 2,969,789 | 1/1961 | Morch | 128/205.24 |
| 4,297,999 | 11/1981 | Kitrell | 128/205.16 |
| 4,354,520 | 10/1982 | Easley, Jr. | 128/205.24 |
| 4,655,213 | 4/1987 | Rapoport et al. | 128/205.25 |

FOREIGN PATENT DOCUMENTS

| | | | |
|---|---|---|---|
| 1256024 | 2/1961 | France | 128/205.13 |
| 1533196 | 7/1968 | France | 128/205.16 |
| 18696 | of 1898 | United Kingdom | 128/205.14 |
| 1550720 | 8/1979 | United Kingdom | 128/205.24 |

*Primary Examiner*—Edgar S. Burr
*Assistant Examiner*—Kimberly Asher

[57] ABSTRACT

The system includes a remote variable volume bellows that is pumped by the rescuers weight, a suction collection option, an oxygen enrichment venturi valve, and a face mask AIDS Protector Valve that is opened and closed by the rescuer's hand. The system, in its normal configuration, allows for a rescuer to pump ventilation air through an air delivery tube into a valve and through the valve into the face mask and lungs of a victim. The pump is a variable volume spring loaded bellows that works for either an infant, child or adult. It can utilize a venturi tube oxygen connector that insures that maximum supplemental oxygen is fed into the air delivery tube. It also has a pressure relief valve to insure that excess pressure is not placed on the victims lungs. When ventilating, an air delivery tube connects to a valve which is opened or closed by the rescuer placing a hand over the exhaust port. This valve can be used by itself, but it has optional inserts for improved performance. One insert is spring loaded and it opens and closes over the air input port to insure that fluids and exhaust air from the victim do not go back into the fresh air line toward the bellows. Another option has separate internal fresh air and exhaust air chambers to ensure that fresh air does not mix with bad air before reaching the face mask. By injecting fresh air and leaving the exhaust port momentarily open, this latter insert can effectively be used to purge bad/toxic air from a face mask prior to the closing of the exhaust port and full ventilation. This bellows and valve system allows a rescuer to easily perform two person CPR on a patient without having fatigue or mouth and lung contact with the victim. The bellows system has a valve system at the normal air input port that can be set to convert the bellows into sucking in air through the air delivery tube. When this tube is attached to a suction fluid collection container the bellows acts as a source of vacuum and allows removal of fluid from a patient.

14 Claims, 8 Drawing Sheets

AIDS PROTECTION VENTILATION SYSTEM

BACKGROUND OF THE INVENTION

This invention relates to a bellows and valve system used to administer ventilation air to a victim, either in conjunction with or without Cardiopulmonary Resuscitation (CPR). The invention ensures that the rescuer does not come in mouth to mouth contact with the victim and air is delivered to the victim in an energy efficient manner. The viral diseases of AIDS, herpes, and hepatitis constitute a continuous threat to all professionals who work with the public at large or with specific sectors of the public known to be carriers of these diseases.

Hospitals and emergency care units currently stock three different sizes of ventilation bags to handle children, infants and adults. Besides this being an extra cost, the emergency vehicles have limited space for all they need to carry and stock. This device is smaller since one bellows can replace three separate bags. Also this device does not require a squeezing pressure performed by wrist muscles and is therefore a physically less tiring device to operate than the currently common Ambu bag.

The threat of catching a disease is so great today, that emergency care workers, when they are away from work, may not stop to assist in an accident because they are not adequately supported with health safety devices for their protection. The fireman, policeman, teachers, nurses, probation officers, etcetera trained in CPR, should have in their cars and where they work, a CPR aid that protects them from contracting any diseases (i.e. AIDS) from the victim. This device is something they could carry with them in their cars.

The following prior U.S. patents relating to this general field constitute all of the prior art known to the applicant. These patents were located through a novelty search made relative to applicant's invention. To make referencing of these patents easy, each patent has been given a single alphabetic designation from A to I. The following Table I summarizes the features of each of these patents. The specific patents are as follows:

A. Knapke, U.S. Pat. No. 1,918,041 1933;
B. Lombard, U.S. Pat. No. 2,535,938 1950;
C. Christman, U.S. Pat. No. 3,229,689 1963;
D. Wilson, U.S. Pat. No. 4,106,502 1978;
E. Monaco etal, U.S. Pat. No. 3,252,457 1966;
F. Spears etal, U.S. Pat. No. 3,043,302 1962;
G. Gunderson, U.S. Pat. No. 4,196,725 1980;
H. Paoluccio etal, U.S. Pat. No. 4,535,765 1985;
I. White etal, U.S. Pat. No. 4,520,811 1985.

form of mouth to mouth interface between rescuer and victim. Patents B,C,D,E,F,G, and H all used a face mask and all but one of those provided for supplemental oxygen. These same patents also involved some form of valve mechanism for air delivery to the victim. However, none of the patents provided the unique features inherent in the patent application. This system, provides for unanswered needs that include a remote variable volume bellows that is pumped by the rescuer's weight, a suction collection option, an oxygen enhance venturi valve, and a face mask valve that is controllable by the rescuer's hand to ensure a safe, open passage way of air both into and out of the victim. A special option allows for the effective purging of bad toxic air exhaled by the victim into the face mask. Currently the only means of handling a victim who has inhaled toxic fumes is to use a passive device—a face mask with holes in the side for ventilation purposes. This device with its toxic insert can be used with such a mask or with a normal fully closed mask.

DESCRIPTION OF THE INVENTION—GENERAL

This invention is composed of a Basic AIDS Protection Valve (APV) Shell, two different optional inserts, a Variable Volume Bellows, air hose, a Venturi Tube Oxygen Connector, and an optional Suction Fluid Collection Container As a system, they provide either positive ventilation to a victim while insuring separation of the rescuer's mouth and lungs from the breath by-products of the victim, or as an emergency fluid suction device. The optional inserts can be used with the Basic APV Shell to allow for either positive purging of toxic air from a face mask or for added equipment contamination protection by closing off the airway tube when positive ventilation is not taking place. The device protects the operator from infectious diseases since there is no requirement to have the operator ventilate using his or her mouth and lungs. This APV system allows one person to perform the classical two person CPR with ease and with no sense of dyspnea. This means that with this device, one person can ventilate a victim every five chest/heart compressions instead of every fifteen compressions as recommended when only one person is present to perform CPR. In essence this system improves the quality of the CPR one person can perform.

The Variable Volume Bellows is designed to be adaptable for either an adult, child, or infant. This one device operates correctly on any patient. The only ancillary part is a basic face mask of the proper size for the infant, child or adult. Such masks are readily available in the market place and they allow endotracheal tube

TABLE I

| | | | Patents Searched | | | |
|---|---|---|---|---|---|---|
| PATENT ALPHA | BAG | BELLOWS | OXYGEN | FACE MASK | MOUTH TO MOUTH | ENDOTRACHEAL |
| A | NO | NO | NO | YES | NO | NO |
| B | YES | NO | YES | YES | NO | NO |
| C | NO | NO | YES | YES | NO | NO |
| D | YES | NO | NO | YES | YES | NO |
| E | NO | NO | YES | YES | YES | NO |
| F | NO | NO | YES | YES | NO | NO |
| G | NO | YES | YES | YES | NO | NO |
| H | NO | NO | NO | NO | YES | NO |
| I | NO | NO | YES | NO | YES | YES |

From this list of patents only patents B,D, and G provided a bellows or air bag for delivery of air to the victim. The patents D,E, H, and I all involved some usage. Because of the three position bellows design, this unit can replace the three sets of different size ventilation bags typically used to accommodate infants, children, and adults.

The Venturi Tube Oxygen Connector portion of this device enhances the input of supplementary oxygen since it creates, via a venturi tube orifice, a low pressure area (vacuum) at the point where oxygen is supplied to the system. If an external tank of oxygen is not available the oxygen port can be sealed off with a stopper. This connector also has a pressure relief check valve to prevent over inflating the lungs of the patient, and a check valve to allow air to pass in only one direction. The bellows of this device are attached to the Venturi Tube Oxygen connector which is then connected to the valve and face mask via an air line. Such an air line can be cut to any length and a normal 24 inch line allows for placing the bellows on the ground/table next to the patient. The length of the air line allows for optimal placement of the bellows. Such placement leads to easy mechanical compression of the bellows by the rescuer's weight.

To ventilate a victim the bellows are pressed with one hand while the other hand presses down on the APV valve to close it and force the bellows air into the victim. Under situations where the patient is on a table, a longer air line can be used and the bellows can be compressed by one's foot.

BRIEF DESCRIPTION OF THE DRAWINGS

FIG. 2A-2 is a sectional view of the Basic APV Shell with the Clear Airway Insert in place showing the ventilation air movement through it when the exit port is covered and the spring compressed:

FIG. 2B-1 is a plan view of the Basic APV Shell with the Clear Airway Insert placed in the open "Exhaust Position":

FIG. 2B-2 is a plan view of just the Clear Airway Insert:

FIG. 2B-3 is a sectional view of the Basic APV Shell with the Clear Airway Inset in place showing the exhaust air movement through it when the exit port is opened:

BASIC AIDS PROTECTOR VALVE

Figure 1A:
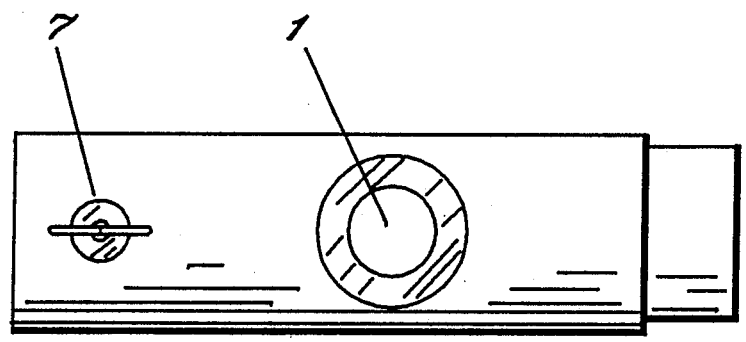
FIG. 1A is a plan view of the Basic APV Shell where no inserts are involved.
Figure 1B:
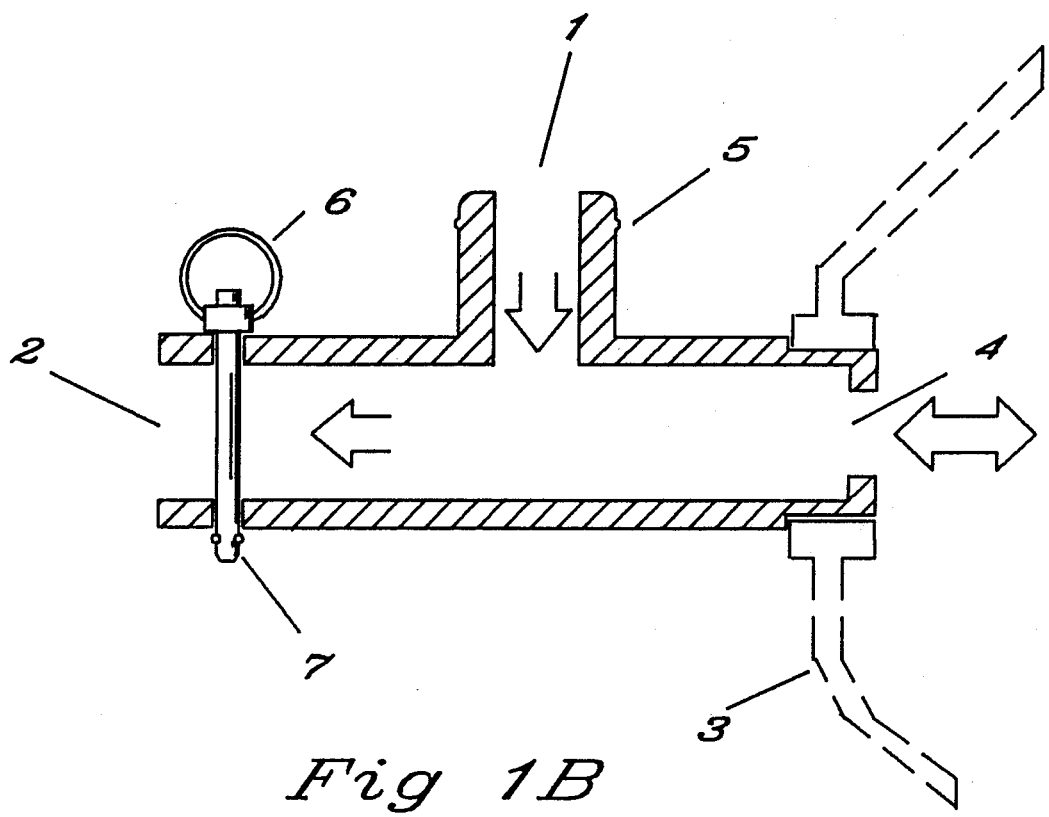
FIG. 1B is a sectional view of the Basic APV Shell from the side.

The AIDS Protector Valve (APV) has a simple "T" shaped Basic APV Shell (FIG. 1) that is a valve with no moving parts. The new ventilation air enters from the bellows through the side port 1, the rescuer closes the exhaust port 2 with a hand, and bellows ventilation air is forced into the mask 3 on the victim through the base 4. The hose from the bellows is connected to this valve by slipping it past the extruded pressure ring 5 surrounding the side port. A latch pin 6, which works in conjunction to the separate inserts, is inserted to simply close off the holes in the case. Plastic gloves are recommended so that as the hand is alternately pressed over the exhaust port 2 during ventilation, there is no risk of body fluids getting into an open cut or scratch on the rescuer's hand. Where the victim has not inhaled toxic fumes or fluids, this system configuration is all that is required to provide safe ventilation to any victim. However, the Basic APV Shell does allow exhaust air to feed into the delivery air hose. Therefore when used without one of the two recommended inserts the operator should first clear any exhaust air from the delivery hose by pumping on the bellows slightly before closing off the exhaust port with a hand. Alternatively the Venturi Oxygen Connector (FIG. 5A) could be provided with reversed male/female ends to allow the end with the flapper valve to be connected to the Basic APV Shell. Such placement would prevent exhaust air returning down the feeder air hose. Use of this Basic APV Shell without one of the inserts is for emergency conditions only, since either insert improves the performance of the valve.

CLEAR AIRWAY TUBE INSERT

Figures 1, 2A:
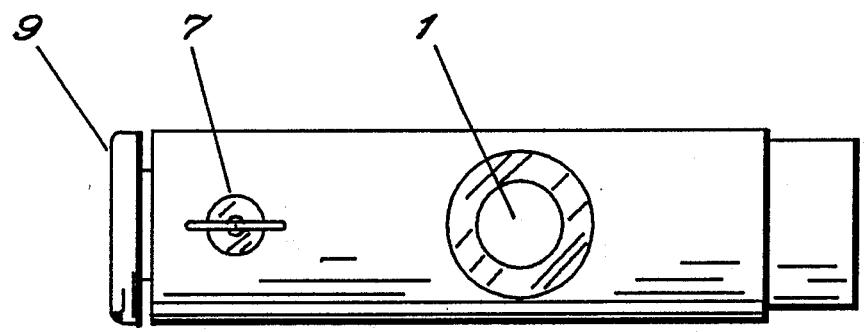
FIG. 2A-1 is a plan view of the Basic APV Shell with the Clear Airway Insert placed in the closed "Ventilate Position"
Figures 2, 2A:
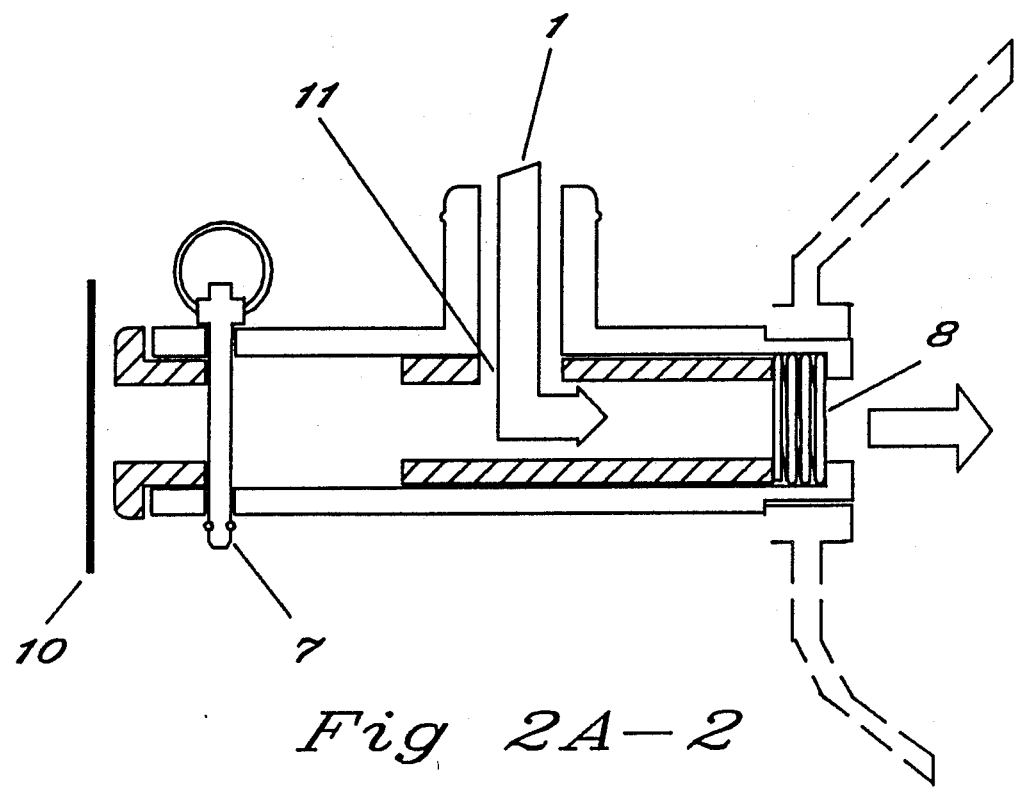
Figures 1, 2B:
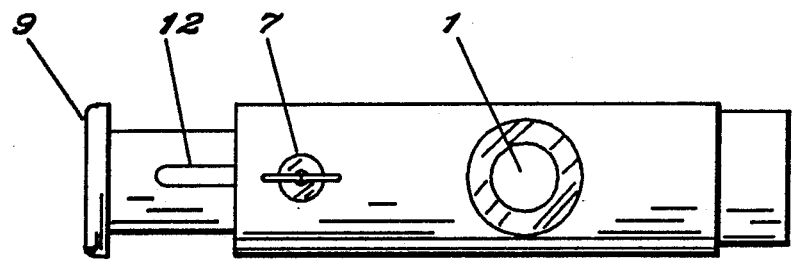
Figures 2, 2B:
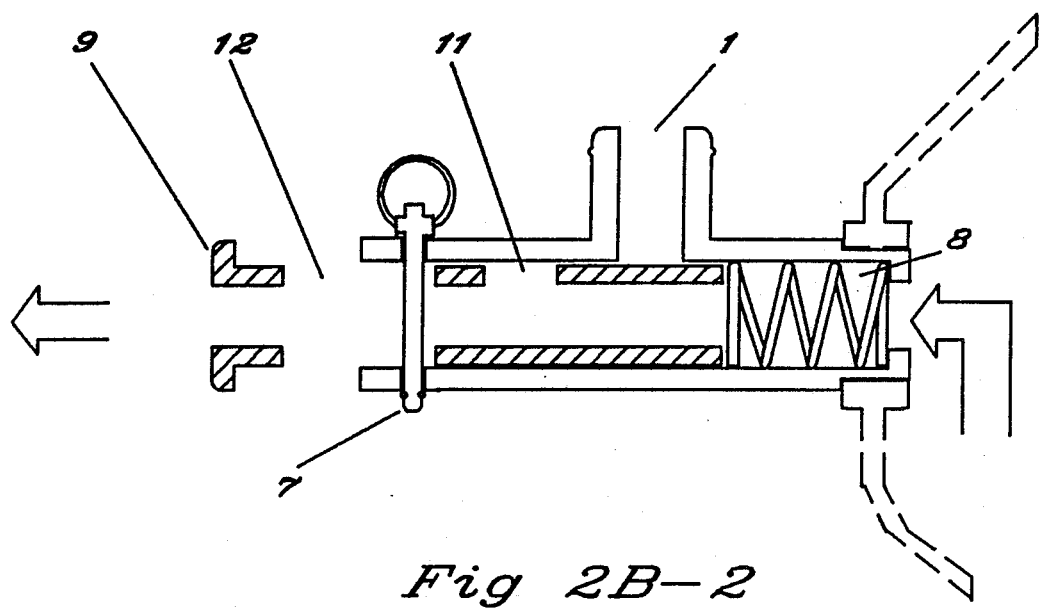

The Basic APV Shell handles two different inserts. FIG. 2A and 2B show how the Clear Airway Insert functions. With any victim but especially with a drowning victim, where significant liquids will be expelled via the mouth, this simple spring loaded valve insert insures that the air passage way to the bellows is shut off except for when the insert is depressed during forced ventilation. To install this insert the latch pin 7 is removed, the spring 8 is inserted, followed by the actual Clear Airways insert 9. As shown in FIGS. 2A and 2B the latch pin 7 is reinserted to hold the insert in place. The Clear Airways Insert can now move up and down inside the Basic APV Shell. When pressure is applied by a rescuer's hand over the exhaust port it closes to the ventilation position. FIG. 2A shows this ventilation phase. The rescuer's hand 10 covers the exhaust port and depresses the insert 9 and spring 8 to cause the air port 11 to be centered over the side port 1 of the Basic APV Shell. The bellows are now depressed forcing air into the victim via the face mask. The hand is removed from the device to create the exhaust configuration as shown in Figure 2B. The slot 12 in the insert holds the insert in place as the spring 8 moves it back up so that the side port to the bellows is blocked. In this exhaust configuration fluids and exhaust gas cannot enter the tube leading from the bellows.

TOXIC AIR INSERT

Figure 3A:
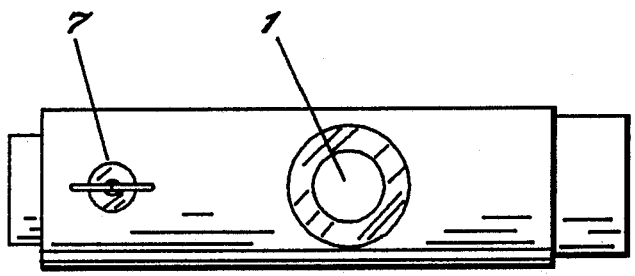
FIG. 3A is a plan view of the Basic APV Shell with the Toxic Airway Insert latched into position.
Figure 3B:
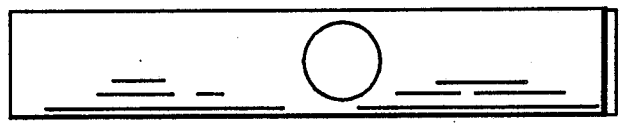
FIG. 3B is a plan view of the Toxic Airway Insert.
Figure 3C:
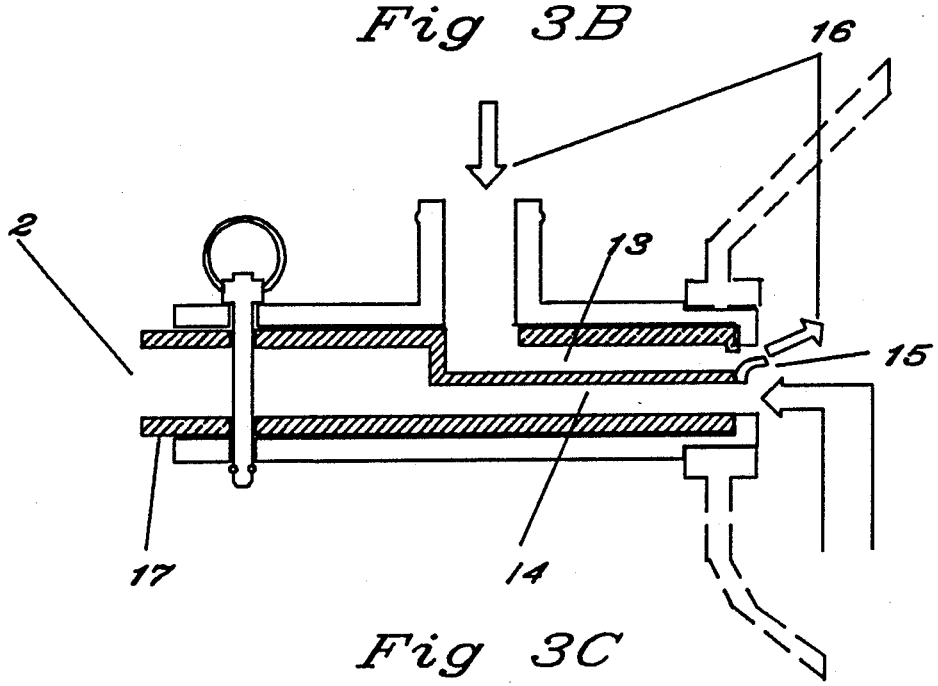
FIG. 3C is a sectional view of the Basic APV Shell with the Toxic Airway Insert in place showing the movement of air through it.

FIG. 3 shows the Basic APV Shell in use with the Toxic Air Insert. This insert does not move but is designed to route the fresh air directly into the face mask. If the operator applies slight pressure to the bellows before closing off the exhaust port 2, then fresh air will flow into the cavity between the victims face and the face mask. In so doing the good air will expel the bad air in the mask by pushing it out through the exhaust port 2. After this momentary purging of the bad/toxic face mask air, the rescuer covers the exhaust port with his hand causing the fresh air to be forced into the victims lungs.

This insert has two inner chambers which keeps the fresh air in chamber 13 separate from exhaust air in chamber 14. At the base of the fresh air chamber is a small flap valve 15 that directs the air 16 to the side and acts to keep fluids and exhaust air out of the inlet chamber during the exhaust cycle. The latch pin holds the insert firmly in place. This insert has a small shoulder 17 existing above the basic APV for two reasons. First it insures an easier port to close off with the hand, and secondly it provides a unique feel and look so that the rescuer knows what type of insert, if any, is in place.

THE VARIABLE VOLUME BELLOWS

Figure 4:
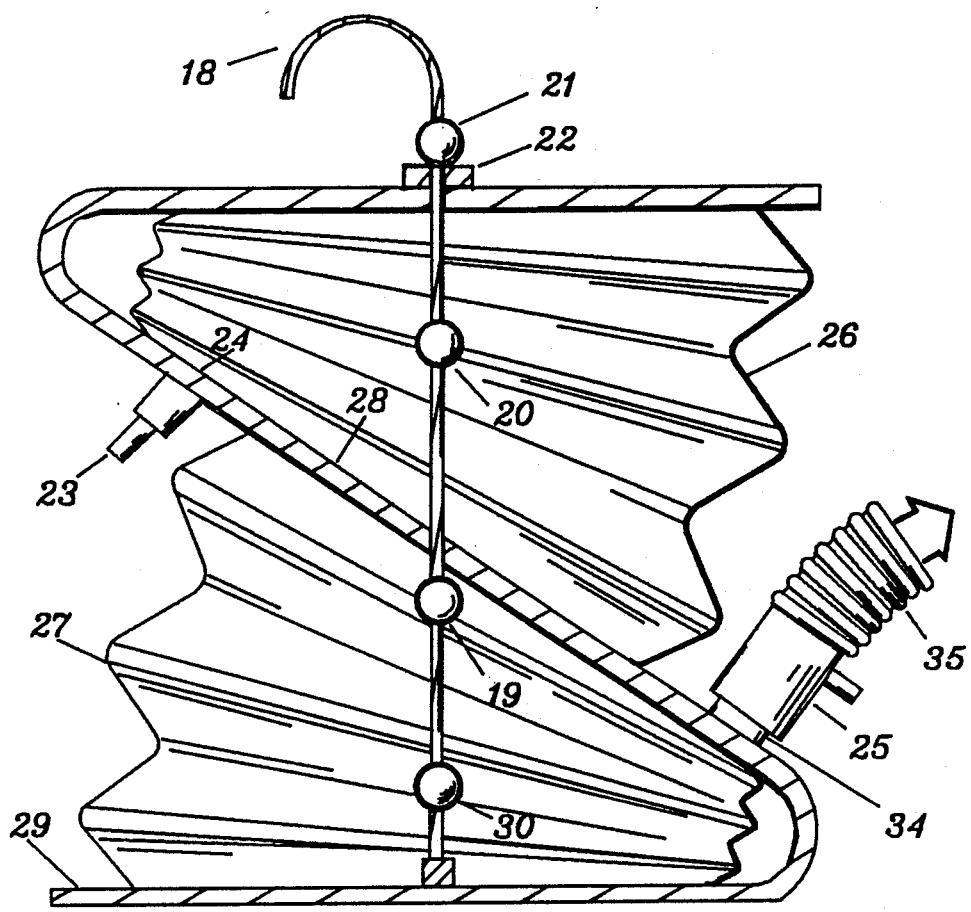
FIG. 4 is a diagram of the Variable Capacity Bellows or suction unit.

FIG. 4 shows one possible configuration of the bellows. The bellows is designed to provide maximum ventilation and volume displacement for its size. This bellows design allows the unit to be compressed to the smallest possible size for storage and transport. Chain(s) 18 (one on each side of frame) in FIG. 4 has four separate hook locations 19,20,21, and 30 which allow the operator to adjust the bellows for use on either an infant, child, adult or for the position used for storage or when used as a vacuum source. Selection of a given volume size is done by hooking the desired volume indicators (parts 19,20, or 21) into notch 22 on both sides of bellows frame. Once the chain is hooked, the bellows are limited to how much they can expand and thus as to how much ventilation air is generated when it is compressed. The bellows are fully expanded for adult ventilation, medium expanded for child usage, and minimum expansion is used for the infant victim.

Opening 23 is the air intake valve to the bellows. To use the bellows to ventilate a victim this valve is open. To use this bellows as a portable suction device this valve is closed after the bellows are compressed. Ventilation air passes from upper bellows 26 to lower bellows 27 through hole 28 in bellows frame 29. Frame 29 is made of aluminum alloy, spring steel, or other suitable material. Upper and lower bellows bladders are made of neoprene, canvas, or similar material. This bellows design has a minimum size footprint or area taken up by its base when it is set on a surface, but with minor modification and a larger footprint, it can be constructed using only the lower bellows bladder section in a larger size. A minimum size footprint means that the total square area occupied on the surface holding the bellows is reduced since the bellows is composed of two bladders that stack on top of each other. In case these bellows are used for suction purposes the bladders are removable for cleaning or disposal. The flapper valve 24 is a membrane that allows air to only pass into the bellows. Output of air from the bellows, is through the Venturi Oxygen Connector 25 which slips over the bellows connector 34 to attach to the bellows. The bellows and Venturi Oxygen Connector are connected to the APV by a flat or round air hose 35 which can be either cleaned and reused, or thrown out and replaced. Flat tube usage is desired when this unit is to be stored where minimizing storage space is important and suction feature is not desired.

VENTURI TUBE OXYGEN CONNECTOR

Figure 5A:
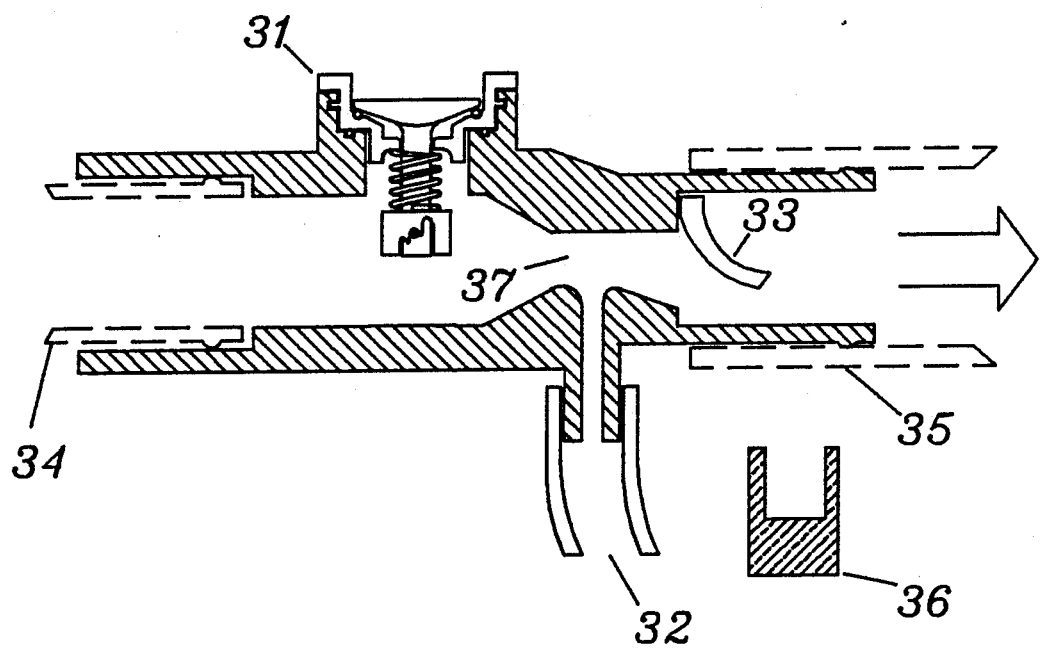
FIG. 5A is the Venturi Type oxygen connector.

FIG. 5A is the Venturi Tube Oxygen Connector which allows for supplemental oxygen to be fed to the victim. The attachment of an oxygen air line enriches the oxygen content of the ventilation air sent to the victim. If oxygen is not available then the input line port of this device is plugged up with a cap 36. A pressure relief valve 31 ( also see FIG. 5B) and flapper valve 33 are built into the Venturi Tube Oxygen Connector which attaches to the hose that feeds air to the APV valve and face mask. The flapper valve 33 ensures that when the bellows is expanding that air is not sucked into the bellows from the air line and APV. The oxygen tube connector is of a size that allows existing oxygen tubing to be attached to it. The Venturi Tube Oxygen Connector is inserted between the bellows and the air line feeding the APV. This connector has a male and female end which allows it to be connected on the female side to the bellows connector 34, and on the male side to the air hose 35 going to the APV. The venturi tube design provides a constriction at point 37 to cause the ventilation air to be at high velocity and therefore at low pressure. At this low pressure point 37 the oxygen 32 is input thus increasing the total quantity of oxygen provided when air is being forced into the patient. Since the flapper valve 33 is between this port and the face mask, further low pressure to this point is provided when air is being sucked in and the bellows is expanding. At this time no air is moving through this part, and the bellows is taking in outside air via the air intake part 23 in FIG. 4, thus creating a vacuum at point 37 of this device and thereby providing even more oxygen enriched air storage. Thus, with this device oxygen is almost constantly being sucked into the bellows.

Figure 5B:
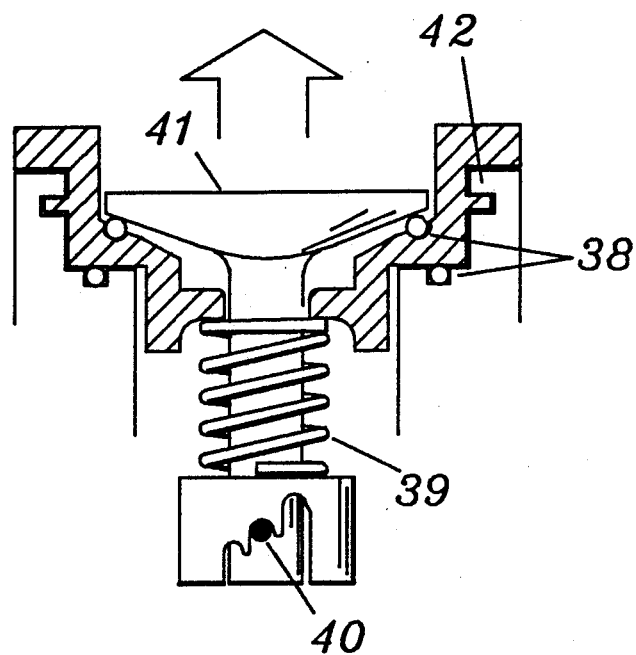
FIG. 5B is an enlarged sectional view of the pressure relief valve.

An adjustable pressure relief valve, FIG. 5B or 31 in FIG. 5A, is provided which allows for controlling the pressure which a compressed spring 39 provides on the relief valve stem 41. This valve is held in place by two twist lock disconnects 42 that allow for its easy and rapid removal or insertion. Once removed a variable position pressure control fitting 40 is available to allow the user to set the spring loading for various over pressure conditions such as are unique for an infant, child or adult. If the internal air pressure overcomes the spring pressure, the valve stem 41 is moved away from the frame and the excess pressure is relieved. The valve stem has "O" ring seals 38 to insure no undesired leakage.

SUCTION FLUID COLLECTION CONTAINER

Figure 6:
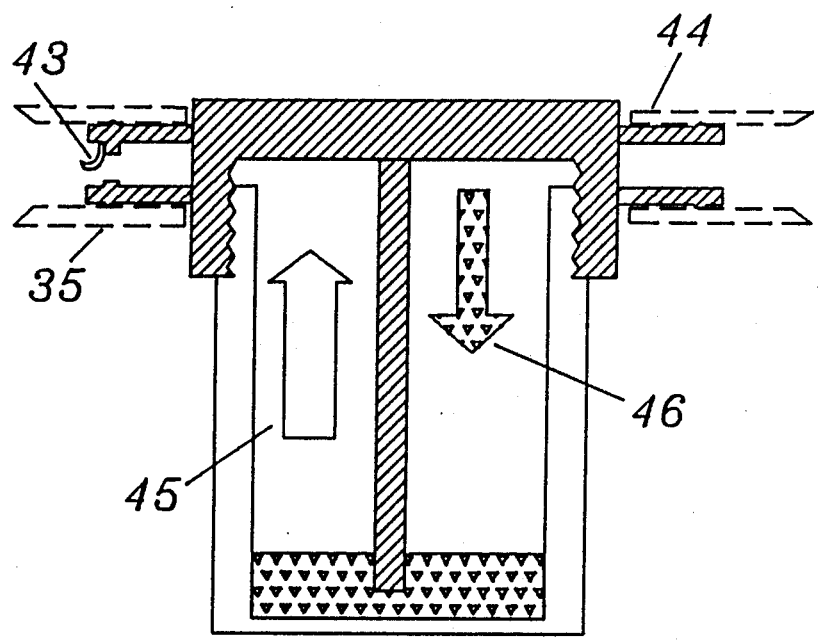
FIG. 6 is the Suction Collection container.
Figure 7:
FIG. 7 is the system in use doing CPR.

FIG. 6 is a Suction Fluid Collection Container which allows for fluids to be removed from a victim by using the bellows in a reverse mode of operation. To use this system in this configuration, the bellows are first locked into the closed position by compressing them and latching them with closed position ball(s) 30 in FIG. 4. The air inlet valve 23 is closed so that air can only enter via the normal exit port. The Oxygen Venturi Tube Connector 25 with its flapper valve 33 in FIG. 5 are removed and a round, non collapsible air delivery hose, is connected directly to the bellows. Next the Suction Fluid Collection Container FIG. 6 is connected to the air line 35 and a new inlet tube 44 which truncates into one of many existing fluid retrieval tubes which are placed into the fluid to be extracted. Finally the straps holding the bellows closed are released and the bellows expand creating a vacuum in the collection container. This suction 45 draws the fluid 46 into the container where it is collected.

Each time another suction cycle is needed the inlet hose is disconnected, the bellows are collapsed and the hose is reconnected. The bellows are then released to create the desired vacuum. Flapper valve 43 is provided as an insurance so that depressing the bellows does not accidentally force collected fluid back into the source from which it was collected.

While the apparatus herein described is the preferred embodiment of the invention, it is to be understood that the invention is not limited to a given precise form.

I claim:

1. An Aids protection ventilation system comprising:
    an adjustable spring loaded variable volume bellows, said bellows being usable to resuscitate a victim, and when used to resuscitate a victim, said bellows creating air pressure which forces air through;
    an air delivery tube having a pressure relief valve and an oxygen inlet port that is connectable to an oxygen source;
    an oxygen enrichment venturi valve that is used to input maximum oxygen into the air provided by said bellows, but, independent as to whether oxygen or said oxygen enrichment venturi valve is utilized the air from the bellows flows through the air delivery tube into;
    a resuscitation airway valve having two ends and adapted to receive one of several optional inserts for improved performance, and a face mask, one end of said airway valve being connectable to said face mask, said face mask being placeable on a victim to supply air to the victim and another end of said airway valve being open to the atmosphere for exhausting the victim's exhaled air or fluid wastes, said another open end of said airway valve being closable by the rescuer's hand when ventilation is needed, said bellows being compressed to force in fresh air from said bellows to the victim's lungs;
    whereby said system in use enables the procedure to be performed without exposing the rescuer's mouth and lungs to the victim's mouth and fluids.

2. The system of claim 1, wherein said rescuer operated adjustable spring loaded variable volume bellows has an air pressure supplying configuration and a suctioning configuration, said bellows in said supplying configuration having three volume settings, wherein said bellows can be set to supply the appropriate volume of air for either an infant, child, or adult;
    when air pressure supply is desired, a force is exerted by the rescuer on said bellows to collapse them and the expelled air is fed through said air delivery tube to the victim for resuscitation purposes;
    said bellows being put in said suctioning configuration by first compression the said bellows, then allowing the spring action of said bellows to expand the bellows to create a vacuum in the connecting air delivery tube, the vacuum being utilized to suction up materials such as fluids.

3. The system of claim 2, having an associated suction collection bottle for use in said air delivery tube when said bellows is used to suction a victim;
    said suction collection bottle having internal baffles, wherein said baffles allows fluids to be suctioned into the bottle, but not into said bellows.

4. The system of claim 3 wherein the suction side of the collection bottle has a flap valve which closes if pressure instead of suction is applied to the container thus preventing any collected fluids from being expelled from the bottle back toward the said bellows.

5. The system of claim 2, further comprising means for varying the length of said air delivery tube between said face mask and said bellows, such that said bellows can be displaced from the victim a distance determined by the location of the victim during resuscitation, i.e. depending upon whether the victim is laying on a table of laying on the ground.

6. The system of claim 2, wherein said bellows comprises multiple sections, said sections being wedge-shaped;
    said sections being stacked on top of each other to increase the bellows internal air displacement volume measurement without increasing the footprint of the bellows; said stackable sections also minimizing the storage volume of the bellows relative to the air displacement capability of the bellows.

7. The system of claim 2, wherein said bellows has an external frame made of spring type material that, when compressed, springs back to its original shape.

8. The system of claim 1, wherein said oxygen enrichment venturi valve increases the amount of oxygen that is mixed in with air that is passed through it for resuscitation purposes;
    said oxygen enrichment venturi valve having a large diameter intake and exit port relative to its center, and a small diameter section into which oxygen is fed, such that the oxygen content is increased due to the laminar flow created by the design of the venturi valve which causes fresh air passing through the venturi valve to be changed from a high pressure-low velocity state in the large diameter entrance area, to a high velocity-low pressure state in the center section at exactly the point the oxygen is fed into the system;
    the resulting low pressure state providing less resistance to the oxygen entering the air delivery line while ensuring a good mixture of oxygen and air in the air delivery line;
    said venturi valve having an exit port, said exit port having a flapper valve that opens when said bellows is compressed to cause air to be passed through said venturi valve towards the victim, but closes when said bellows is expanded to draw in air, and because said air delivery line is closed by the flapper valve during the bellows expansion/suction cycle, the low pressure in the bellows is also present at said oxygen inlet port during the suction cycle.

9. The system of claim 1, wherein said pressure relief valve is used to relieve over-pressure conditions and has a variable pressure control means having three settings, said pressure control means being easily changed between over-pressure relief settings for an infant, child, or an adult.

10. The system of claim 9, wherein said three settings of said variable pressure controller of said pressure relief valve are pre-calibrated to correspond to over-pressure relief points for an infant, child, and an adult.

11. The system of claim 10 where said pressure relief valve has means for easily removing said pressure relief valve from said air delivery line to allow for rapid changes in overpressure requirements, said means for easily removing said pressure relief valve comprising a twist-lock disconnect being used to insert and hold said pressure relief valve in place, said pressure relief valve further comprising an over-pressure exhaust port, said pressure relief valve having means for being set in one of said three settings, said means comprising a mushroom valve, an O-ring seal, a spring, a slotted ring, and a spring shaft having a knob, said pressure relief valve being held in one of said three positions by having said mushroom valve held down against said O-ring seal by said spring that is held in compression with said slotted ring where the slots of the ring are of various lengths and where said knob on the spring shaft can be hooked thus allowing the spring to be compressed to various preset distances or pressure settings such that if the over-pressure exerted on the mushroom valve is greater than the spring force, as compressed by the slotted ring, the valve will open.

12. The system of claim 1, wherein said airway valve comprises:
- a T-valve, where one end of the T-valve inserts into and connects onto a victim's face mask, an end opposite said one end is open to the atmosphere and forms an exhaust port, and a side port providing a fresh air intake port having a means to connect to said air delivery tube which receives air from a separate source and where said T-valve can be utilized without any inserts;
- said exhaust port being open to allow the victim to exhale, and being covered by the rescuer's hand when air is being supplied to the victim.

13. The system as recited in claim 12, wherein said airway valve is adapted to receive and accept one of a plurality of inserts;
- A. a positive air displacement insert comprising a tube having a separation chamber down the middle from the fresh air intake port to the face mask, and a check valve, said check valve preventing the direct mixture of exhaled and fresh air in said airway valve; said positive air displacement insert, when combined with coordinated use of said air delivery system and the removal of the rescuer's hand over the exhaust port of the airway valve, allowing for the expelling of accumulated toxic or exhaled air from the face mask through the exhaust port before fresh air is forced into the mask cavity and onto the victims lungs; or
- B. a hollow spring loaded movable insert having an opening in the side to allow pressurized fresh air to enter the airway valve when the spring loaded insert is depressed, but when said spring loaded insert is not depressed, said opening is closed to prevent exhaled air or liquid in the airway valve from mixing with fresh air in said air delivery tube; said spring loaded insert being used by having the rescuer alternately depress said spring loaded insert to close off the end of the spring loaded insert and to allow fresh air to enter through the side opening and thus be supplied to the victim; and release said spring loaded inset to close said side opening and thereby open said airway tube from the face mask to the atmosphere to allow for the exhaust of exhaled air from the victim'lungs.

14. The system of claim 12, wherein said airway valve includes means enabling insertion and use of an endotracheal tube inside of the face mask.

* * * * *